United States Patent [19]

Stark

[11] Patent Number: 5,146,094
[45] Date of Patent: Sep. 8, 1992

[54] MEDICAL DIAGNOSTIC NUCLEAR CAMERA SYSTEM

[75] Inventor: Iain E. Stark, Dollard des Ormeaux, Canada

[73] Assignee: Isis Inc., Quebec, Canada

[21] Appl. No.: 712,352

[22] Filed: Jun. 7, 1991

[51] Int. Cl.[5] .................. G01T 1/166; A61B 6/03
[52] U.S. Cl. .................. 250/363.08; 250/363.04; 250/363.05; 250/363.10; 378/148
[58] Field of Search ............ 378/148; 250/505.1, 250/363.02, 363.03, 363.04, 363.05, 363.08, 363.09, 363.10; 128/653.1, 653.4, 654, 659

[56] References Cited

U.S. PATENT DOCUMENTS

| | | |
|---|---|---|
| 3,624,398 | 11/1971 | Arndt . |
| 3,982,133 | 9/1976 | Jupa et al. . |
| 4,088,889 | 5/1978 | Meixner . |
| 4,109,155 | 8/1978 | Tschunt et al. . |
| 4,129,784 | 12/1978 | Tschunt et al. . |
| 4,220,861 | 9/1980 | Colombo et al. . |
| 4,221,971 | 9/1980 | Burger .................. 378/148 |
| 4,241,254 | 12/1980 | Valila . |
| 4,365,342 | 12/1982 | Vepy . |
| 4,445,035 | 4/1984 | Ueyama .................. 250/363.04 |
| 4,459,485 | 7/1984 | Span . |
| 4,460,832 | 7/1984 | Bigham . |
| 4,517,460 | 5/1985 | Meulenbrugge et al. ... 250/363.09 X |
| 4,541,108 | 9/1985 | Grady et al. . |
| 4,645,933 | 2/1987 | Gambini et al. . |
| 4,649,277 | 3/1987 | Terra et al. . |
| 4,652,759 | 3/1987 | Platz . |
| 4,692,625 | 9/1987 | Hanz et al. . |
| 4,694,481 | 9/1987 | Tashijan et al. . |
| 4,716,581 | 12/1987 | Barud . |
| 4,741,015 | 4/1988 | Charrier . |
| 4,758,726 | 7/1988 | Douma et al. .................. 250/505.1 X |
| 4,774,411 | 9/1988 | Span . |
| 4,774,412 | 9/1988 | Kurkake . |
| 4,809,313 | 2/1989 | Gandolfo . |

FOREIGN PATENT DOCUMENTS

| | | | |
|---|---|---|---|
| 58-30685 | 2/1983 | Japan | 250/363.04 |
| 59-178382 | 10/1984 | Japan | 250/363.04 |
| 63-90787 | 4/1988 | Japan | 250/363.04 |
| 2-263185 | 10/1990 | Japan | 378/148 |

Primary Examiner—Constantine Hannaher
Assistant Examiner—Edward J. Glick
Attorney, Agent, or Firm—Darby & Darby

[57] ABSTRACT

The nuclear scintillation camera system has an improved positioner including a drum which is rotatable on a frame which may be linearly moved along a track. The camera is cantilevered to the drum and is able to rotate about the axis of the cantilever as well as about an axis perpendicular to the axis of the cantilever and parallel to the plane of the camera crystal. The frame may be moved along the track with the camera in a given position for doing linear body scans, and with the patient positioned along the axis of the drum, scans around the patient may be carried out for emission computed tomography (ECT). The system also provides a collimator changer stand for exchange and storage of collimeters for use with the nuclear scintillation camera. The system according to the invention makes nuclear scintillation imaging easier to carry out.

14 Claims, 7 Drawing Sheets

MEDICAL DIAGNOSTIC NUCLEAR CAMERA SYSTEM

FIELD OF THE INVENTION

The present invention relates to a medical diagnostic nuclear camera system. The invention relates further to a mechanical positioner and to a collimator changer for a medical diagnostic nuclear camera system.

BACKGROUND OF THE INVENTION

In prior art nuclear or scintillation cameras, the vertical travel of a detector or camera has been achieved either by counterbalancing the detector about a pivot or a motor driven screw jack. This causes problems in various areas of normal clinical operations including the possibility of varying the total weight of the detector, raising or lowering the detector and maintaining the focus of the collimator at the same point. The ability to perform complex motions around a patient and view a constant slice of the patient is compromised, along with the precision and reproduceability of the motions.

While such scintillation camera systems have existed for about two decades now, performing to a greater or lesser degree satisfactorily, the advances and resolutions in newer systems have created greater demands in precision alignment between the camera and the patient support.

In general, all known nuclear camera systems, whether or not including emission computed tomography (ECT) capability, feature a counterbalanced detector, with an inherent flexure of the structure and a variable viewing point in the patient due to the radius from the pivot to the detector, or a toe or forward projecting structure to stabilize the medical diagnostic positioner. The systems inherently suffer flexure due to the permissible dimensions of the structural sections and high concentrations of structural loadings, leading to inaccuracies in reproducible positioning. The loss of resolution and contrast of the imaging device, the scintillation camera detector head, arises from mechanical flexure in the rotating cantilever structure supporting the scintillation detector or camera head and from a lack of position alignment between the bed and the detector head, particularly during rotation of the camera head. A nuclear camera system capable of both whole body static imaging as well as emission computed tomography or ECT, is the Gemini system available from General Electric Corporation, Milwaukee, Wis., and described in U.S. Pat. No. 4,651,007 (Perusek et al.). U.S. Pat. Nos. 4,645,933 (Gambini et al.) and 4,692,625 (Hanz et al.) also describe medical diagnostic detector support systems having rotating cantilevered structures.

In the prior art nuclear or scintillation cameras, the exchange and storage of collimators has been accomplished by movements of the gantry and manually exchanging the collimators. A collimator for a nuclear camera is a nuclear radiation absorbing and focussing screen having a mass between 10 and 100 kilograms. The collimators for nuclear cameras have an array of parallel holes which provide the one to one correspondence between the emission of the pattern of radiation from the patient to the pattern of individual detectors of the detector crystal. The collimators are usually made of lead and have particular characteristics most suited to the patient study and the energy of emission of the radio-pharmaceutical agent ingested by the patient. This defines that the collimators will not be of the same weight, if they encompass the energy range and have the optimum geometry for the particular application.

Previously, collimators were stored on individual trolleys or a storage rack. In the former case, the trolleys are positioned under the detector head of the scintillation camera and the detector head is lowered onto the collimator and the collimator is fixed to the detector head by bolts or similar means. In the latter case, a mobile trolley lifts the collimator from the rack, the trolley is moved to the detector head where it is lowered onto the detector and fixed by bolts or similar means. Both systems function in a satisfactory degree to a greater or lesser extent.

More recently, automatic collimator changers for scintillation cameras have been proposed which operate on a swivel exchange mechanism for exchanging the collimators. U.S. Pat. Nos. 3,982,133 (Jupa et al.), 4,109,155 (Tschunt et al.) and 4,129,784 (Tschunt et al.) are examples of such collimator exchangers.

OBJECTS OF THE INVENTION

It is an object of the invention to provide a medical diagnostic nuclear camera mechanical positioner capable of supporting a nuclear scintillation camera detector without instability. It is a further object of the invention to provide a multi-purpose mechanical diagnostic imaging support structure which simplifies the structure of the mechanical positioner, provides entirely independent motions on all axes of the detector as well as very precise and reproducible motions while allowing for static, linear and rotational imaging, such as by a rotatable scintillation detector. It is also an object of the present invention to provide a collimator changer for a scintillation camera which is able to provide a smooth, easy and safe exchange of collimators automatically.

SUMMARY OF THE INVENTION

The present invention provides a medical diagnostic nuclear camera system comprising: a nuclear scintillation camera; positioner track means providing an elongated linear path of travel; a positioner frame unit rotatably supporting a cylindrical shell drum and mobile on the positioner track means along the path, the drum having an axis which is horizontal and perpendicular to the path; mounting means connected to one end of the drum for supporting the camera, the mounting means able to rotate the camera about an axis parallel to the axis of the drum; counterweight means connected to an opposite end of the drum diametrically opposite the mounting means for substantially balancing a weight of the camera such that a center of gravity of the positioner frame unit lies stably over the positioner track means; frame drive means for moving the positioner frame unit along the path on the positioner track means; drum drive means for rotating the drum; mounting drive means for causing the mounting means to rotate the camera; means provided on the camera for slideably receiving and fastening a collimator in a plane parallel to a front surface of the camera; a collimator storage stand having a plurality of collimator holders vertically disposed one above the other, for holding a plurality of collimators, the collimator storage stand being positioned near an end of the positioner track means, the camera positionable in front of the stand; collimator track means provided at each collimator holder for slideably holding one of the collimators in each holder and for allowing one collimator held in each holder to slide from the holder to the means for slideably receiving and fastening; and collimator drive means for linearly moving the collimator between the holder and the camera, whereby when the camera is moved by the frame drum and mainting drive means to the stand, the means for slideably receiving and fastening can be aligned with the collimator track means of one of the plurality of collimator holders. The collimator drive means may therefore exchange a collimator between the camera and the collimator storage stand.

The invention also provides a medical diagnostic nuclear camera mechanical positioner comprising: track means providing an elongated linear path of travel; a main frame unit rotatably supporting a cylindrical shell drum and mobile on the track means along the path, the drum having an axis which is horizontal and perpendicular to the path; mounting means connected to one end of the drum for supporting the camera, the mounting means able to rotate the camera about an axis parallel to the axis of the drum; counterweight means connected to an opposite end of the drum diametrically opposite the mounting means for substantially balancing a weight of the camera such that a center of gravity of the main frame unit lies stably over the track means; frame drive means for moving the main frame unit along the path on the track means; drum drive means for rotating the drum; and mounting drive means for causing the mounting means to rotate the camera.

And, the invention also provides a collimator changer for scintillation camera, the camera having means for slidably receiving and fastening a collimator in front of the camera, the changer comprising: a collimator storage stand having a plurality of collimator holders vertically disposed one above the other for holding a plurality of collimators; track means provided at each collimator holder for slideably holding one of the collimators in each holder and for allowing the collimator held in the holder to slide between the holder and the means for slideably receiving and fastening; and drive means for moving the collimator held in the holder along the track means between the stand and the camera.

DETAILED DESCRIPTION OF THE PREFERRED EMBODIMENT

Figure 1:
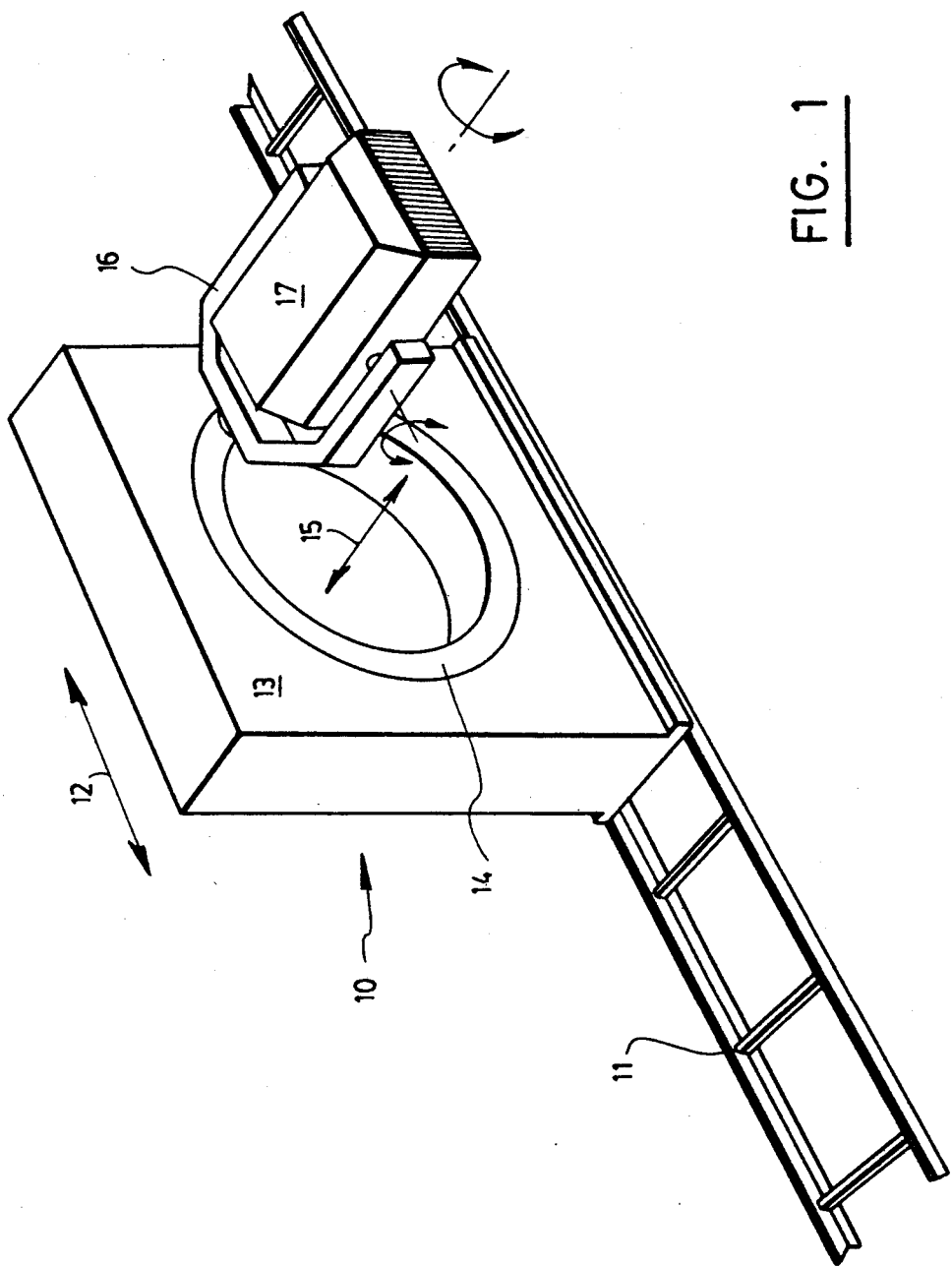
FIG. 1 is a perspective view of a medical diagnostic mechanical positioner according to a preferred embodiment.

As shown in FIG. 1, the medical diagnostic nuclear camera mechanical positioner (10) has a track (11) which provides an elongated linear path (12) along which a main frame unit (13) can travel. The main frame unit (13) rotatably supports a cylindrical shell drum (14). The drum (14) has an axis (15) which is horizontal and perpendicular to the path (12). Mounting means (16) support a camera (17) and are connected to one end of the drum (14) and are able to rotate the camera about an axis parallel to axis (15) of drum (14).

Figure 2:
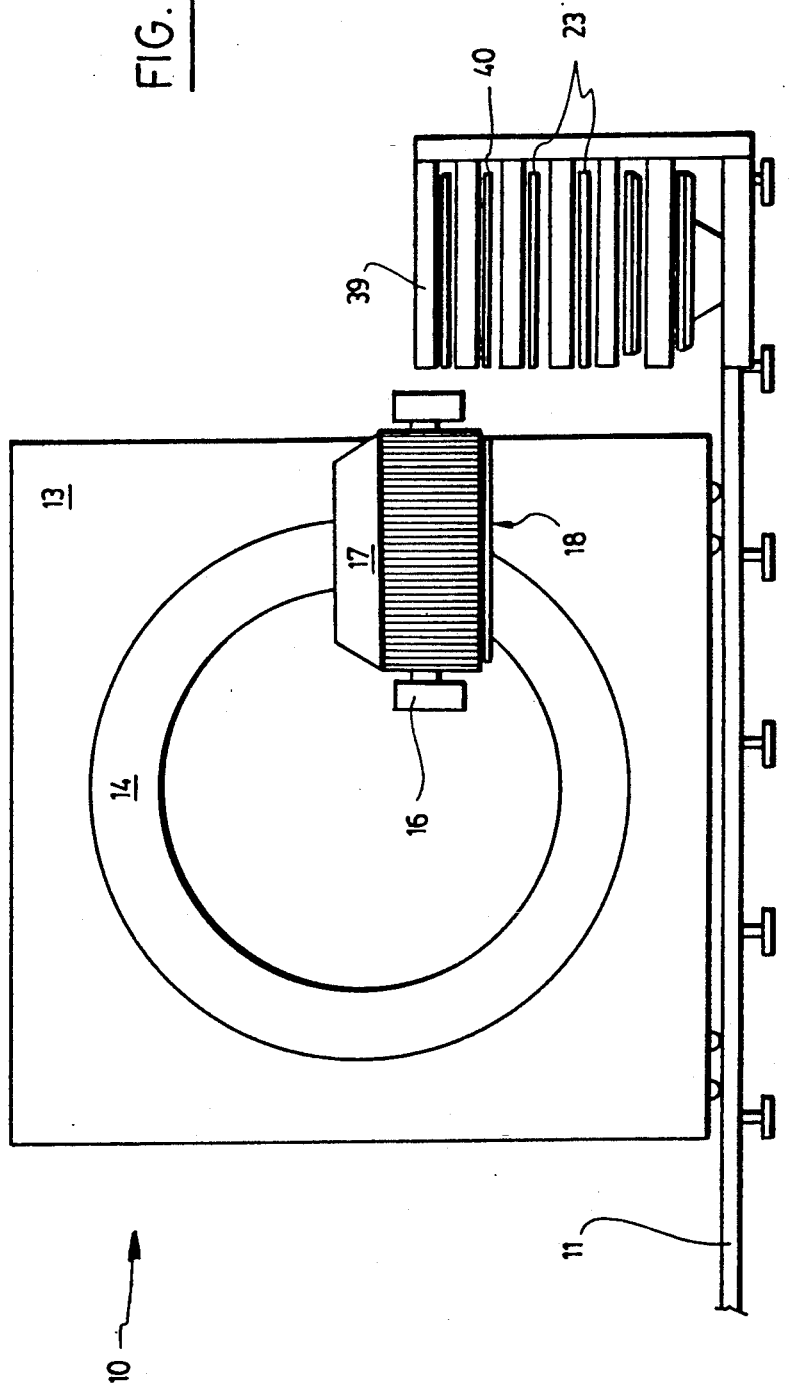
FIG. 2 is a side view of a medical diagnostic nuclear camera system including the mechanical positioner and a collimator changer for the scintillation camera showing the collimator changer placed at a side of the camera for ease of illustration.

As can be understood from FIG. 1, camera (17) may be rotated about axis (15), may be moved linearly along path (12), and the mounting means (16) may rotate the camera (17) about an axis parallel to axis (15) and about an axis perpendicular to axis (15) and parallel with an aperture surface (18) of camera (17) (as shown in FIG. 2). The heavy camera (17) is cantilevered only a short distance from its support on drum (14) and all basic linear and rotational movements can be provided with ease of control and a simplified structure.

Figure 3:
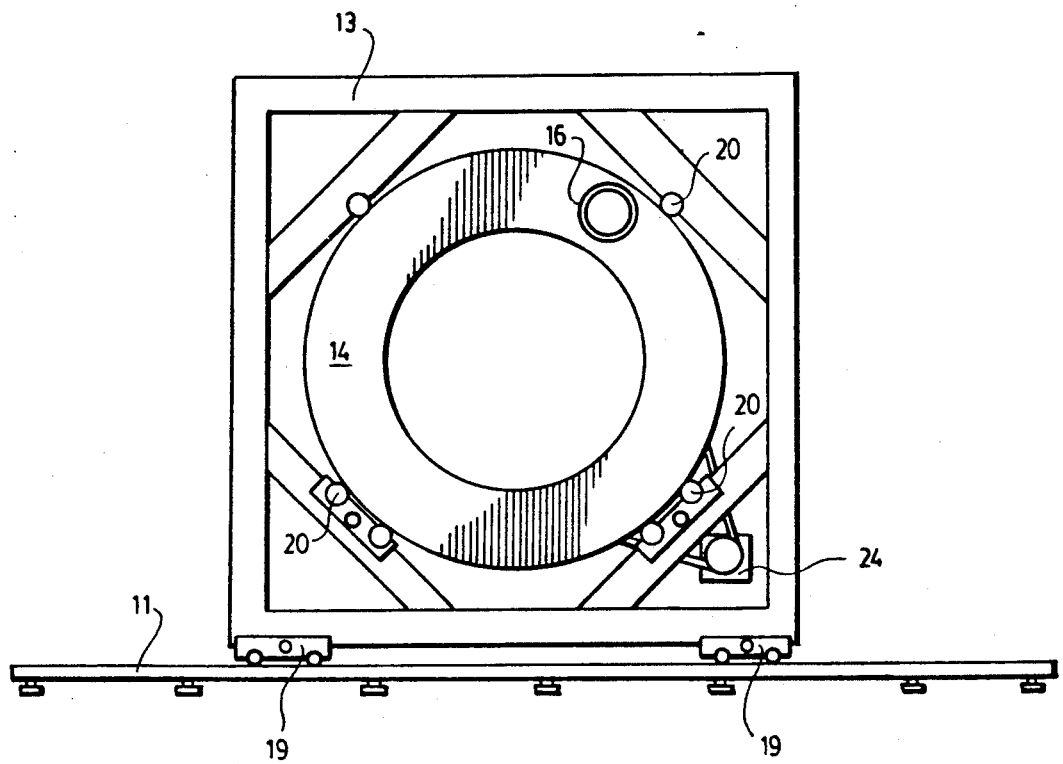
FIG. 3 is a side view of the mechanical positioner of FIG. 2 with the cover plates and nuclear camera removed in order to show the rotating drum and associated drive means.
Figure 4:
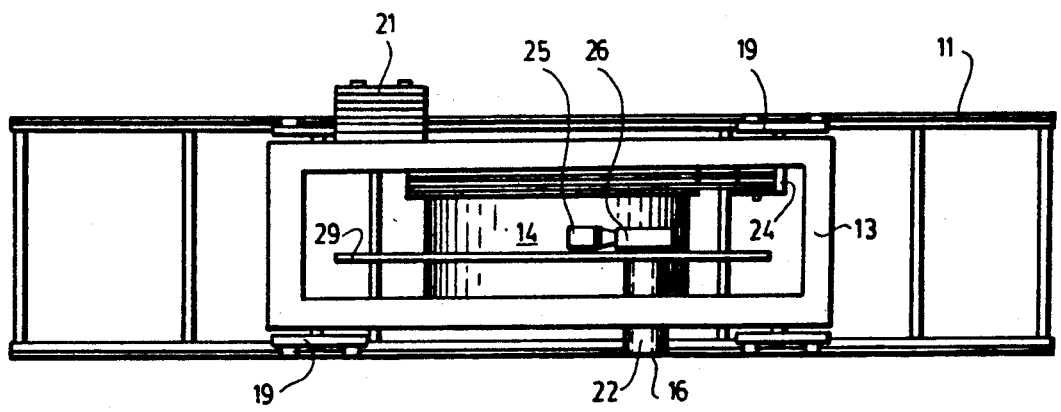
FIG. 4 is a top view of the mechanical positioner as shown in FIG. 3.

With reference to FIGS. 3 and 4, it can be seen that main frame unit (13) is provided with a number of trucks (19) which roll along the track (11) for linear movement along path (12). Drum (14) is supported by rollers (20) at the bottom and top in order to allow drum (14) to rotate within frame (13). The trucks (19) preferably comprise V-wheels such as those available from Bishop-Wisecarver of Pittsburg, Calif. The surface of the rails of track (11) is made preferably of hardened steel, and the track (11) can be mounted on either adjustable pads or bolts set into the floor.

A counterweight (21) is provided diametrically opposite the support member (22) of mounting means (16) and provides a sufficient counterbalance so as to place the center of gravity of drum (14) containing mounting means (16) and camera (17) close to the center of track (11) when camera (17) supports an average weight collimator (23). Drum (14) is rotated by drum drive means (24). The supporting member (22) is rotated by a motor (25) connected to a gearreduction box (26).

Figure 5:
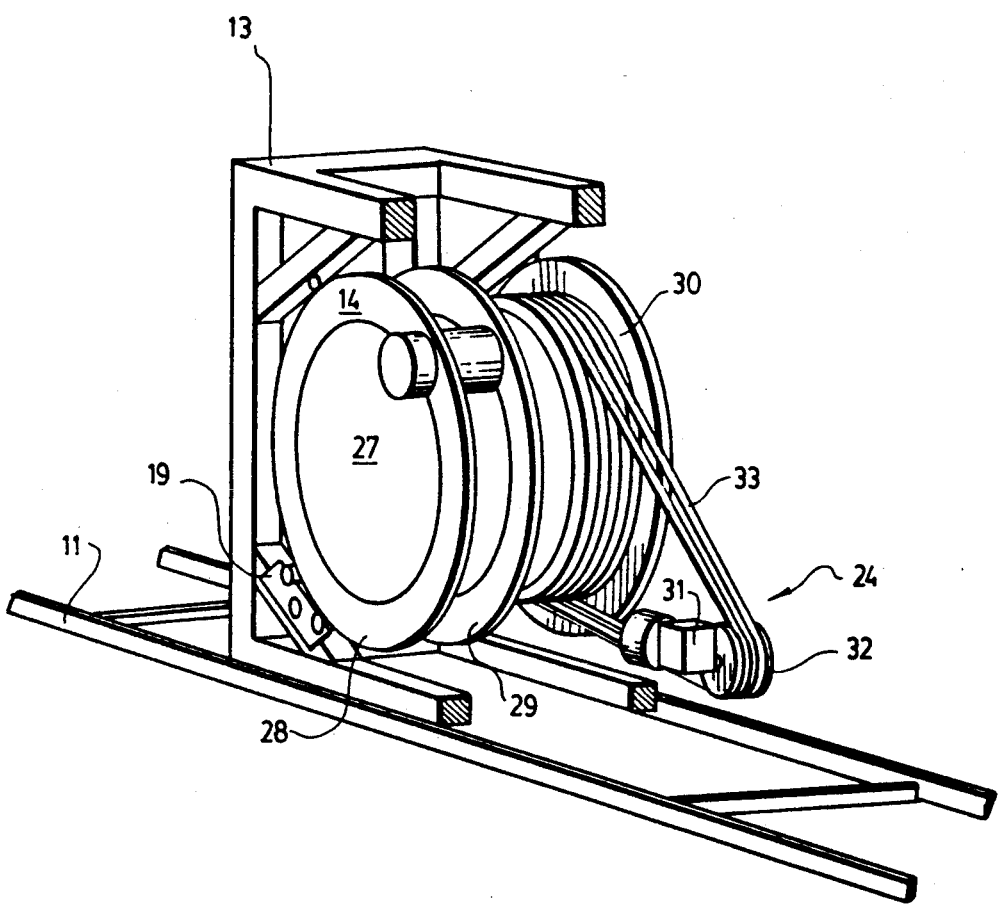
FIG. 5 is an oblique partially cut-away view of the mechanical positioner shown in FIG. 3.
Figure 6:
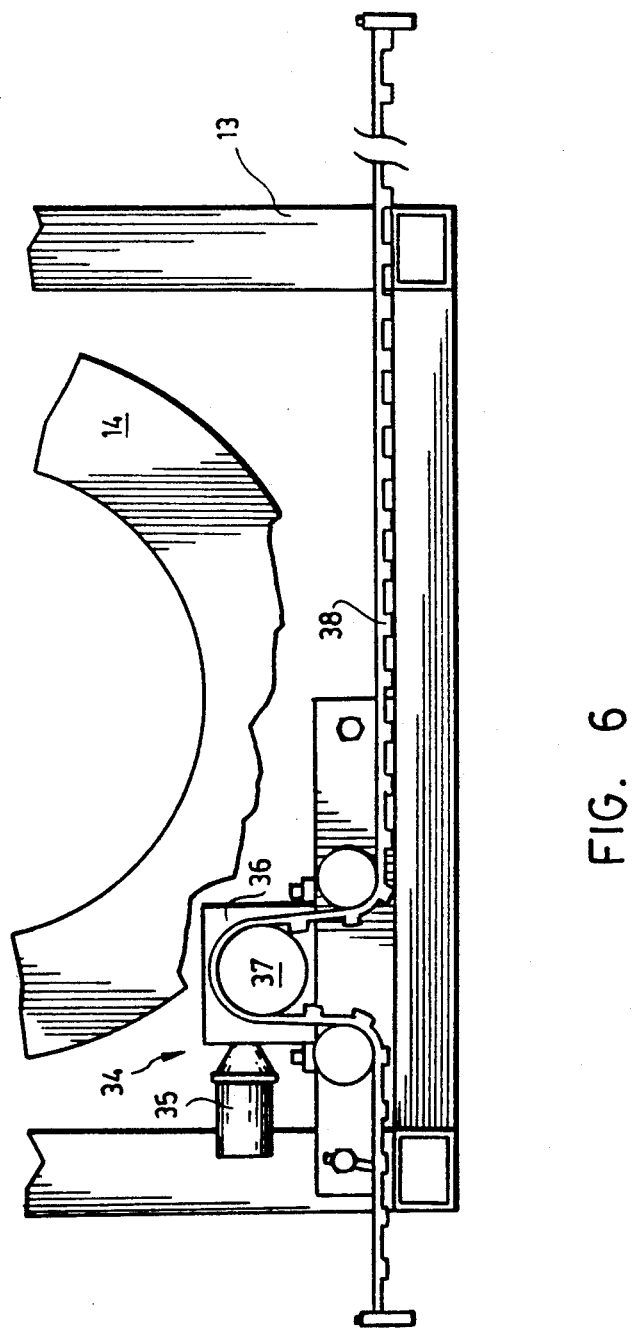
FIG. 6 is an enlarged cut-away view showing the frame drive means used for linearly moving the mechanical positioner frame unit along its track.

As shown in FIGS. 5 and 6, drum (14) includes a cylindrical shell body (27) on which three annular disks (28), (29) and (30) are mounted. A first one (28) of the disks is located on the camera side, a second one (30) of the disks is mounted on the counterweight side and a third one (29) of the disks is mounted centrally on body (27). The cylindrical support member (22) is rotatably mounted on disks (28) and (29) and the drum drive means (24) are provided to engage the drum between disks (29) and (30). The drum drive means (24) include a motor with gear-reducing box (31) which drive a pulley (32) and a belt or belts (33) for engaging a specially adapted surface of body (27).

The frame drive means (34) include a motor (35) connected to a gear-reduction box (36) for driving a pulley (37) which is in working engagement with a timing belt (38) for being able to provide a precise linear movement along path (12).

Figure 7:
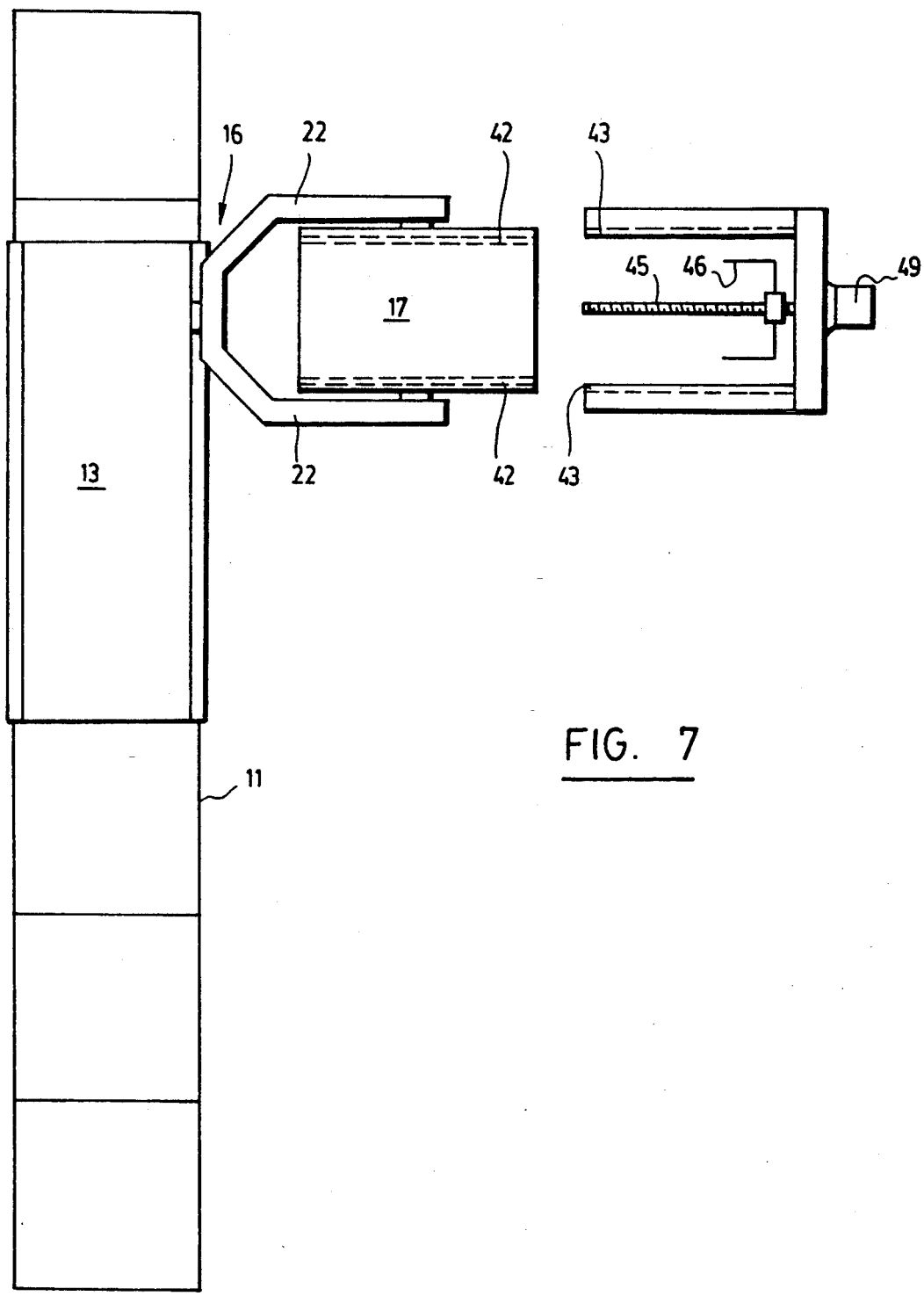
FIG. 7 shows a top view of the mechanical positioner supporting the scintillation camera detector head in position to exchange a collimator with the collimator changer.

With reference to FIGS. 2 and 7, it is shown how the mechanical positioner (10) can be used to place nuclear camera (17) in line with collimator storage stand (39) which has a plurality (six shown in FIG. 2) of collimator holders (40) vertically disposed one above the other for holding a plurality of collimators (23) and a precalibrated radioactive source (41) having a form similar to the collimators (23). Camera (17) has an aperture surface (18) over which collimator (23) is to be placed. Camera (17) can be adjusted in height by rotating drum (14) and support member (22) in order to bring surface (18) in line with holder (40). As shown in FIG. 7, the stand (39) is located in front of camera (17).

Figure 8:
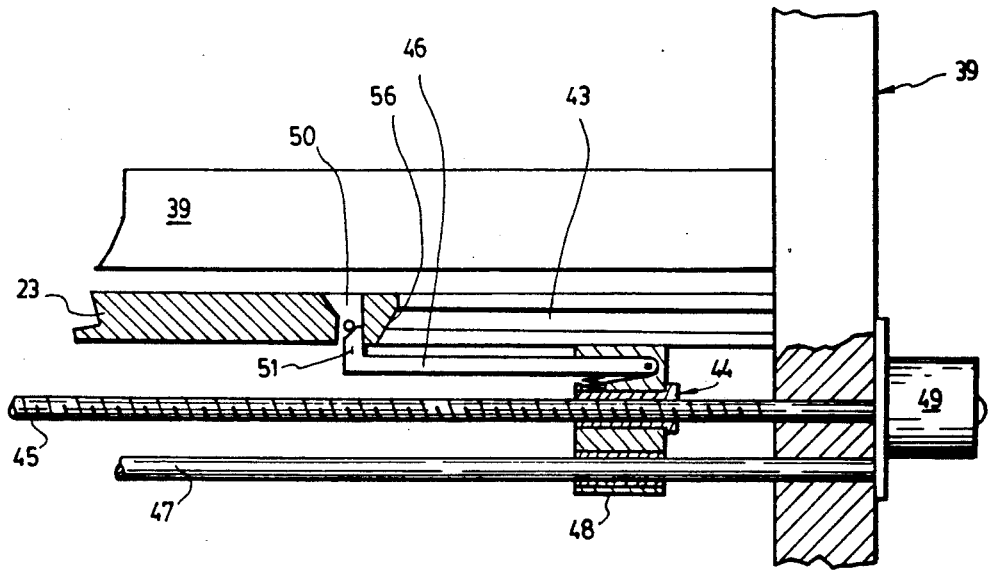
FIG. 8 shows a detailed break-away view of the collimator changer drive means.
Figure 9:
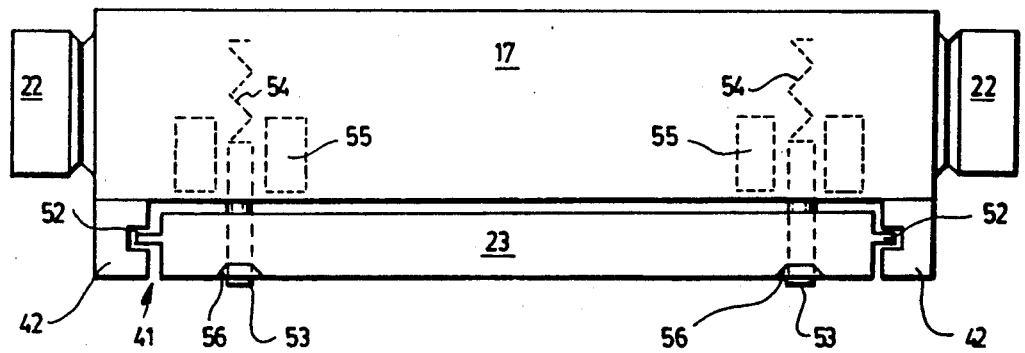
FIG. 9 shows an enlarged view of a collimator mounted on the scintillation camera detector and the solenoid release mechanism.

As shown in FIGS. 7 through 9, the camera aperture surface (18) is provided with means (41) for receiving and fastening a collimator (23) in front of surface (18). In the preferred embodiment, the collimators (23) are provided with tongues made of UHM plastic which slide along grooves also made of UHM plastic of holders (40) and onto grooves (42) made of UHM plastic of means (41). Holders (40) are each provided with two grooves (43), one on each side, which correspond with a pair of grooves (42) of the means (41) provided on camera (17).

It is important that grooves (42) and (43) are brought into accurate alignment so that the tongues of the collimator can slide in the grooves (42), (43) with ease between the camera (17) and the stand (39).

FIG. 8 shows a cross section of the collimator drive means which comprise feed screw means (44) for each collimator holder (40). The feed screw means (44) include a feed screw shaft (45), a smooth shaft (47) parallel to the feed screw shaft (45), a locking member (46) for hooking into collimator (23). Nut member (48) has threads for engaging the feed screw shaft (45) and has a slide for engaging the smooth shaft. The locking member (46) is pivotally attached to the nut member and is resiliently biased in the vertical direction. The nut member (48) may be moved along the feed screw shaft and the smooth shaft by rotation of the feed screw shaft (45) by means of motor (49). The locking member (46) is forked and has two prongs for engaging complementary receiving notches (50) of collimator (23). Ends (51) of member (46) may only engage notches (50) when the solenoid release mechanism shown in FIG. 9 is activated.

In FIG. 9, there is shown an end view of camera (17). Collimator (23) is slidable in slots or grooves (42) and (43) by tongues (52). The collimator locking rods (53) are maintained in a secure position in collimator locking notches (50) by springs (54) and may only be retracted by energizing solenoids (55). The solenoids (55) are fixed to a front end of camera (17). The collimator (23) has guide slots (56) for guiding the spring biased retracting members (46). Thus, members (46) cannot engage collimator (23) unless solenoids (55) are activated and locking rods (53) are moved out of notches (50) allowing ends (51) to enter notches (50).

The advantage of the locking means described is that the release of collimator (23) requires energising the releasing solenoids (55) and that connection and disconnection of the hook members (46) is controlled by the action of solenoids (55).

It is to be understood that the above description is not intended to limit the scope of the invention as defined in the appended claims.

What is claimed is:

1. A medical diagnostic nuclear camera mechanical positioner comprising:

track means providing an elongated linear path of travel;

a main frame unit rotatably supporting a cylindrical shell drum and mobile on the track means along said path, the drum having an axis which is horizontal and perpendicular to said path;

mounting means connected to one end of the drum for supporting the camera, the mounting means able to rotate the camera about an axis parallel to said axis of the drum;

counterweight means connected to an opposite end of the drum diametrically opposite the mounting means for substantially balancing a weight of the camera such that a center of gravity of the main frame unit lies stably over the track means;

frame drive means for moving the main frame unit along said path on the track means;

drum drive means for rotating the drum; and mounting drive means for causing the mounting means to rotate the camera.

2. The mechanical positioner as claimed in claim 1, wherein said mounting means is further able to rotate the camera about an axis perpendicular to said axis of the drum and parallel to a plane surface of an aperture of the camera.

3. The mechanical positioner as claimed in claim 1, wherein the drum comprises an inner cylindrical body and three annular disks, an interior diameter of said disks fitting over said cylindrical body, a first and second of said disks being placed at respective ends of the cylindrical body and a third of said disks being placed centrally on said cylindrical body, and wherein the main frame unit is provided with roller means for rotatably supporting at least the first and second of said disks in order to rotatably support the drum.

4. The mechanical positioner according to claim 3, wherein the mounting means include a support member rotatably seated in the first and third of said disks.

5. The mechanical positioner as claimed in claim 1, wherein the frame drive means include an electric motor provided on the main frame unit, said electric motor being connected via gear reduction means to a pulley which is operatively connected to an open ended timing belt provided on the track means, whereby activation of said motor can move the main frame unit along said path on the track means.

6. The mechanical positioner as claimed in claim 3, wherein the drum drive means include a belt engaging said cylindrical body, said belt being driven by a pulley connected to gear reduced motor means for rotating the drum.

7. The mechanical positioner as claimed in claim 4, wherein the mounting drive means include an electric motor which is coupled by gear reduction means to said support member.

8. A collimator changer for a scintillation camera, the camera having means for slideably receiving and fastening a collimator in front of the camera, the changer comprising:

a fixed position collimator storage stand having a plurality of collimator holders vertically disposed one above the other for holding a plurality of collimators;

track means provided at each said collimator holder for slideably holding one of said collimators in each said holder and for allowing the collimator held in said holder to slide between said holder and said means for slideably receiving and fastening, the track means being fixed to each said holder; and drive means for moving said one of said collimators held in each said holder along said track means between said stand and said camera, the drive means being able to drive said one of said collimators from the track means across a gap between said stand and said camera to a final position in said means for slideably receiving and fastening, and vice versa.

9. A collimator changer as claimed in claim 8, wherein said drive means comprise feed screw means provided at each said holder for engaging said collimators and linearly moving said collimators along said track means.

10. A collimator changer as claimed in claim 9, wherein the feed screw means comprise a feed screw shaft, a smooth shaft parallel to the feed screw shaft, a locking member for engaging on said collimators, a nut member having threads for engaging the feed screw shaft and having a slide for engaging the smooth shaft, the locking member being pivotally attached to the nut member and resiliently biased in a vertical direction, whereby the nut member may be moved along the feed screw shaft and the smooth shaft by rotation of the feed screw shaft, and the locking member may engage a complementary receiving member of said one of said collimators in order to move said one of said collimators whenever said means for slideably receiving said collimator provided on the camera release said one of said collimators and permit engagement of the locking member with the complementary receiving member of said one of said collimators.

11. A medical diagnostic nuclear camera system comprising:

a nuclear scintillation camera;

positioner track means providing an elongated linear path of travel;

a positioner frame unit rotatably supporting a cylindrical shell drum and mobile on the positioner track means along said path, the drum having an axis which is horizontal and perpendicular to said path;

mounting means connected to one end of the drum for supporting the camera, the mounting means able to rotate the camera about an axis parallel to said axis of the drum;

counter weight means connected to an opposite end of the drum diametrically opposite the mounting means for substantially balancing a weight of the camera such that a center of gravity of the positioner frame unit lies stably over the positioner track means;

frame drive means for moving the positioner frame unit along said path on the positioner track means;

drum drive means for rotating the drum;

mounting drive means for causing the mounting means to rotate the camera;

means provided on the camera for slideably receiving and fastening a collimator in a plane parallel to an aperture surface of the camera;

a collimator storage stand having a plurality of collimator holders vertically disposed one above the other, for holding a plurality of collimators, the collimator storage stand being positioned near an end of the positioner track means, the camera positionable in front of said stand;

collimator track means provided at each said collimator holder for slideably holding one of said collimators in each said holder and for allowing said one collimator held in each said holder to slide from said holder to said means for slideably receiving and fastening; and collimator drive means for linearly moving said collimator between said holder and said camera, whereby when said camera is moved by the frame drum and mainting drive means to said stand, the means for slideably receiving and fastening can be aligned with the collimator track means of one of said plurality of collimator holders, so that the collimator drive means may exchange a collimator between the camera and the collimator storage stand.

12. A system as claimed in claim 11, wherein the collimator drive means comprise feed screw means, the feed screw means including a locking member for connecting with the collimators, and the means for slidably receiving and fastening including locking means for locking said collimators in front of the camera and for preventing the locking member from engaging said collimators when the locking means is in a locked state, and for allowing said collimators to slide toward the collimator track means and allowing the locking member to engage said collimators when the locking means are in a disengaged state.

13. A system as claimed in claim 12, wherein the feed screw means comprise a feed screw shaft; a smooth shaft parallel to the feed screw shaft, a nut member having threads for engaging the feed screw shaft and having a slide for engaging the smooth shaft, the locking member being pivotally attached to the nut member and resiliently biassed in a vertical direction, whereby the nut member may be moved along the feed screw shaft and the smooth shaft by rotation of the feed screw shaft, and the locking member may engage a complementary receiving member of said collimators in order to move the collimators whenever said locking means release the collimators and permit engagement of the locking member with the complementary receiving member of the collimators.

14. A scintillation camera system as claimed in claim 11, wherein one of said plurality of holders contains a precalibrated radioactive source having a form similar to said collimators.

* * * * *